US006584848B1

(12) United States Patent
Yost et al.

(10) Patent No.: US 6,584,848 B1
(45) Date of Patent: Jul. 1, 2003

(54) NON-DESTRUCTIVE EVALUATION METHOD EMPLOYING DIELECTRIC ELECTROSTATIC ULTRASONIC TRANSDUCERS

(75) Inventors: William T. Yost, Newport News, VA (US); John H. Cantrell, Jr., Williamsburg, VA (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 0 days.

(21) Appl. No.: 10/263,292

(22) Filed: Sep. 30, 2002

Related U.S. Application Data

(60) Provisional application No. 60/371,799, filed on Apr. 11, 2002.

(51) Int. Cl.[7] .................. G08B 13/00; G01N 29/04; G01N 9/24
(52) U.S. Cl. .......................... 73/645; 73/643
(58) Field of Search ................ 73/643, 645, 602; 310/311

(56) References Cited

U.S. PATENT DOCUMENTS

| 5,287,331 A | * | 2/1994 | Schindel et al. ............ 367/140 |
| 5,566,573 A | * | 10/1996 | Yost ............................. 73/643 |
| 6,443,901 B1 | * | 9/2002 | Fraser ......................... 600/459 |

* cited by examiner

Primary Examiner—Helen Kwok
Assistant Examiner—Tamiko Bellamy
(74) Attorney, Agent, or Firm—Helen M. Galus

(57) ABSTRACT

An acoustic nonlinearity parameter ($\beta$) measurement method and system for Non-Destructive Evaluation (NDE) of materials and structural members novelly employs a loosely mounted dielectric electrostatic ultrasonic transducer (DEUT) to receive and convert ultrasonic energy into an electrical signal which can be analyzed to determine the $\beta$ of the test material. The dielectric material is ferroelectric with a high dielectric constant $\in$. A computer-controlled measurement system coupled to the DEUT contains an excitation signal generator section and a measurement and analysis section. As a result, the DEUT measures the absolute particle displacement amplitudes in test material, leading to derivation of the nonlinearity parameter ($\beta$) without the costly, low field reliability methods of the prior art.

13 Claims, 2 Drawing Sheets

NON-DESTRUCTIVE EVALUATION METHOD EMPLOYING DIELECTRIC ELECTROSTATIC ULTRASONIC TRANSDUCERS

This application claims the benefit of Provisional application Ser. No. 60/371,799, filed Apr. 11, 2002.

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

1. Field of the Invention

The present invention generally relates to ultrasonic measurement techniques for non-destructive evaluation (NDE) of materials and structural members, including the determination of fatigue damage. More particularly, the present invention relates to improved ultrasonic-based approaches to determining the nonlinearity parameter ($\beta$) for assessing the fatigue damage to structural members.

The fields of use include, inter alia, ultrasonic fatigue sensor technology, process monitor technology for optimum strength of materials, bond strength analysis technology, and other nonlinear acoustic data information technology.

2. Background

NDE of materials involves the inspection of materials without having to damage the materials or dismantle structures to which the materials are incorporated. Among the many important NDE operations are the inspection of aircraft, bridge, and building structural members to detect fatigue damage that could possibly lead to catastrophic failure, as well examining bonds (e.g., adhesive junctions) between members for indications of prospective failure.

Prior art methods of fatigue damage detection include bombarding material under test with acoustic finite amplitude waves in the ultrasonic range, and examining, via a transducer, the response waves (including the fundamental and harmonics) produced by the material to determine a nonlinearity parameter ($\beta$) which may be correlated to material fatigue.

One prior art approach of note requires that a piezoelectric transducer be bonded directly to the material being tested. The test material is excited by introducing finite-amplitude ultrasonic waves perpendicular to the surface of the test material, whereupon the surface vibration energy is received by the transducer and analyzed to determine the nonlinearity parameter ($\beta$). Among the drawbacks of this approach is the fact that the results must be corrected for the layer of bond material between the test material and the transducer, and it is assumed that the test,material and transducers are both flat and parallel. Further, the attenuation characteristics of the test material must also be known. This approach is therefore impractical at times, and can lead to over-correction (assuming that corrections can be practically made), and therefore inconsistent results.

Another approach of note uses an air-gap capacitive transducer. That is, the surface of the test material serves as part of an air-gap capacitive transducer, with the surface being "free." The direction of acoustic wave propagation is ideally perpendicular to the test material surface, although corrections can be made if the relative wave propagation angle is known. While this approach generally works well if the parameters are carefully controlled, as in a laboratory, it does not work reliably, for example, if the test material surface is not optically flat. Therefore, it is not a practical approach for most field testing of structures.

Yet another approach of note known as laser interferometry impinges laser light on the surface of a vibrating test material. The reflected light is analyzed, employing for example, Michelson or Fabry-Perot demodulation techniques, by complex and often expensive equipment. While a strong approach, it requires that the test material have good optical reflection characteristics, which is not the case for many in-field structures. Additionally, the equipment must be optically aligned (due to temperature and other environmental changes) often to produce reliable results. Those skilled in the art will also appreciate that the excitation waves must be aimed so that the reflection energy exits the surface vibrations precisely in the center of the sound field, which is extremely difficult to locate in practice.

What is therefore needed but sorely lacking in the prior art, is an ultrasonic transducer method of NDE that is reliable in the field, does not require a highly optically reflective test material surface, is cost-effective, and requires minimal preparation of the test equipment and test material in the field.

SUMMARY OF THE INVENTION

In view of the aforementioned problems and deficiencies of the prior art, the present invention provides a system for measuring acoustic nonlinearity ($\beta$) in test materials. In at least one embodiment, the system can at least include an acoustic signal generator adapted to apply an acoustic signal to a test material, a dielectric electrostatic ultrasonic transducer (DEUT) comprising a plate member and a dielectric member coupled to the plate member, the dielectric member being a high dielectric constant insulator, and being adapted to convert received ultrasonic energy into an output electrical signal, and a measurement system coupled to the DEUT, the measurement system being adapted to calculate the nonlinearity $\beta$ in response to the output signal from the DEUT. The DEUT is adapted to be loosely mounted to a surface of the test material, and the DEUT is adapted to receive acoustic energy from the surface of the test material.

The present invention also provides a method of measuring acoustic nonlinearity ($\beta$) in test materials. The method can at least include the steps of generating and applying an acoustic signal to a test material, providing a DEUT comprising a plate member and a dielectric member coupled to the plate member, the dielectric member being a high dielectric constant insulator, and being adapted to convert received ultrasonic energy into an output electrical signal, and loosely mounting the DEUT to a surface of the test material. The method further can at least include the steps of via the DEUT, receiving acoustic energy from the surface of the test material, and via a measurement system coupled to the DEUT, calculating the nonlinearity $\beta$ in response to the output signal from the DEUT.

BRIEF DESCRIPTION OF THE DRAWINGS

Features and advantages of the present invention will become apparent to those skilled in the art from the description below, with reference to the following drawings, in which.

DETAILED DESCRIPTION OF THE INVENTION

The description below details the present-inventive reference-based acoustic measuring system and technique. General discussions of acoustic wave testing for fatigue determination can be found in the following U.S. Patents, all of which name one or both of the inventors for the present letters patent, and the reader is therefore so referred for background material: U.S. Pat. Nos. 5,736,642; 5,566,573; and 5,325,339.

As described in the "Summary," supra, the present-inventive ultrasonic NDE approach novelly employs a DEUT for the conversion of sonic energy into an AC electrical signal to be analyzed for derivation of the nonlinearity parameter ($\beta$). The DEUT is loosely mounted to the structure under test after the test material surface is cleaned (including rust removal if necessary). That is, essentially the only touching between the surface of the dielectric portion of the DEUT and the surface of the test material is at the asperities of the two surfaces. It should be noted that the term "loosely mounted," as used in both the instant specification and claims, it meant to cover a variety of situations, both temporary and permanent. For example, the DEUT may be simply laying on the surface of the structure, or it may be mounted slightly spaced from the surface (but essentially parallel).

Figure 1:
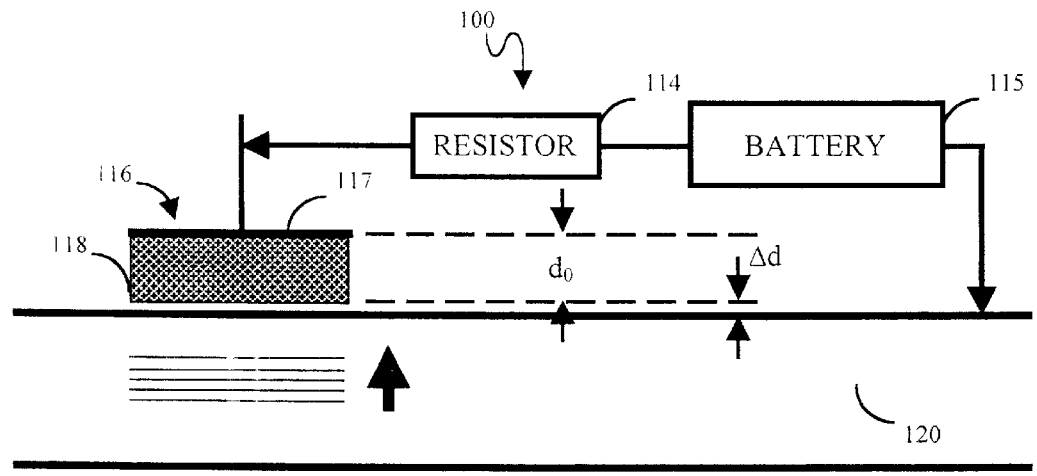
FIG. 1 is a side view of a present-inventive dielectric electrostatic ultrasonic transducer mounted according to the description in this letters patent.

A basic DEUT and arrangement compatible with the present invention are shown in FIG. 1. In the arrangement 100, the DEUT 116 has a flat plate conducting member 117 attached to a ferroelectric insulator 118 having a high dielectric constant/coefficient. The dielectric material 118 may be composed of one of a number of suitable materials that will be known to those skilled in the art, including but not limited to poled ceramic, Lead Zirconate Titanate (PZT), polyvinyl alcohol acetate, HEVEC compound, Forsterite ceramic material, and Barium Titanate.

One side of the test material 120 is bombarded by ultrasonic waves from a sonic generator (not shown). The DEUT is given a DC bias voltage $V_b$ via a bias supply resistor 114 and a bias supply 115, such as a battery also connected to the test material as shown in FIG. 1, the connection being sufficient to provide a good electrical contact. In FIG. 1, $d_0$ represents the distance from the free end, or "bottom," of the dielectric material 118 to the plate 117 of the DEUT, while $\Delta d$ represents the distance between the free end of the dielectric material 118 and the surface of the test material 120.

Figure 2:
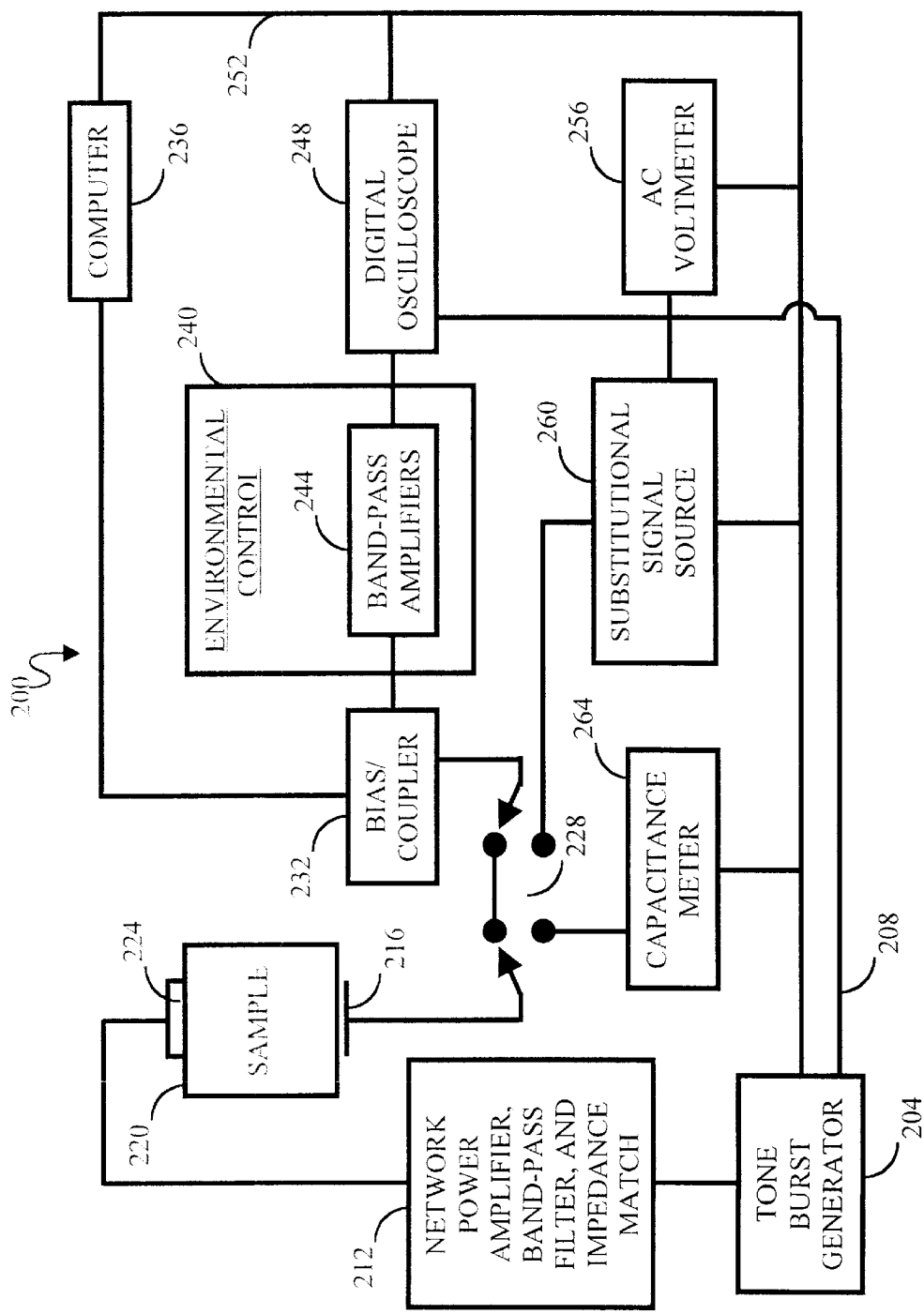
FIG. 2 is schematic block diagram of a present-inventive acoustic signal generation and measurement system.

FIG. 2 is a schematic block diagram showing the present-inventive system 200 for determining the nonlinearity parameter ($\beta$) of a test material sample 220 using a DEUT 216. The system 200 is generally divided into an excitation section and a measurement section. The excitation section contains a tone burst generator 204 (such as Hewlett-Packard Model 3314A) for generating a series of different amplitude tone bursts, for example, in one embodiment, the generator 204 could generate a series of ascending sequential amplitude tone bursts, followed by interleaved descending sequential amplitude tone bursts. As shown, the output of the tone burst generator 204 is processed by a network 212 consisting of: a power amplifier (such as ENI Model A-300); a suitable band pass filter (such as a high power 5 Megahertz (MHz) bandpass filter); and an impedance-matching network (such as MFJ Versatuner 989C).

The electrical signal output from the network 212 is converted into the acoustical waves applied to the test sample 220 by a transducer 224, such as a Lithium Niobate 5 MHz compressional transducer.

The measurement section, responsible for measuring the DEUT output and calculating $\beta$, is under computer control 236. The amplitude A of the displacement measured by the DEUT 216 can be given by $$A=(s_0v)/(2V_b) \quad (1)$$

where $s_0$ is the effective gap spacing, v is the AC output voltage, and $V_b$ is the DC bias voltage.

Equation 1 is derived in the following manner with reference to FIG. 1. The capacitance between the plate 117 and the bottom of the dielectric material 118 ($C_1$) and the capacitance between the bottom of the dielectric material 118 and the surface of the test material 120 ($C_2$) are given by $$C_1=\epsilon S/d_0$$

$$C_2=\epsilon_0 S/\Delta d \quad (2)$$

where $\epsilon$ is the permittivity (also having a dielectric constant K) of the DEUT, and $\epsilon_0$ is the permittivity of air, and S is the surface area of the plate 117, which is the same as the area of the bottom, or free end, surface of the dielectric material 118. The reciprocal of the equivalent capacitance C of the test arrangement is given by $$1/C=1/C_1+1/C_2 \quad (3)$$

Therefore $$1/C=(s_0/\epsilon_0 S)(1+\Delta d/s_0) \quad (4)$$

where $s_0=d_0/K$, and is the effective gap spacing.

Placing a charge Q on the capacitor plate gives the voltage V across the capacitor as V=Q/C or $$V=(Qs_0/\epsilon_0 S)(1+\Delta d/s_0) \quad (5)$$

For an ultrasonic tone burst that causes $\Delta d$ (which can also be written as $\partial(\Delta d)$), the change in voltage $\Delta V$ is given by $$\Delta V=V[1/(1+\Delta d/s_0)][\Delta(\Delta d)/s_0] \quad (6)$$

If $\Delta d/s_0$ is assumed to be very small since the dielectric material is located on the asperities of the test material surface, then $$\Delta V=V[(\Delta(\Delta d)/s_0] \quad (7)$$

For the particle displacement amplitude A resulting from an ultrasonic wave, and given that $\partial\Delta d=2A$, the following is derived for the AC output voltage v of the DEUT $$v=(2AV)/s_0 \quad (8)$$

which is a version of Equation 1.

The bias component of the AC signal from the DEUT 216 is separated from the DC bias component by a bias/coupler 232. An environmental control circuit 240 can be used to isolate the amplitudes of the AC signal(fundamental, harmonics). This environmental control circuit 240 can contain among other things, a bandpass amplifier circuit 244 and filters for the fundamental and desired harmonics, and/or a tunable filter, covering the desired ranges, could be used. Once isolated, the amplitudes of the AC signal are then output to a digital oscilloscope 248 by, for example, activating the appropriate bandpass amplifier in the circuit 244. The analog output signal can either be digitized (e.g., with an analog-to-digital converter) in the environmental control circuit 240 or by the digital oscilloscope 248 or by the computer 236. In one embodiment, the oscilloscope 248 is of the 10 bit, 100 mega samples per second variety, such as the LeCroy Model 9430. The oscilloscope measures the received signals and allows the nonlinearity parameter ($\beta$) to be calculated (for example, by the computer 236, using the following equation $$\beta = \Gamma M_L \quad (9)$$

where $\Gamma$ is the ratio of second harmonic amplitude $A_2$ to the square of the fundamental amplitude $A_1$. ($\Gamma = A_2/A_1^2$), and $M_L = 8c^2/(\omega^2 a)$, where c is the velocity of compressional waves in the test material (which may be obtained from materials handbooks and the like), $\omega$ is the angular frequency, and a is the path length. In practical application, the fundamental and second harmonic particle displacement amplitudes are expected to be in the range of $10^{-9}$ and $10^{-11}$ meters, respectively. To provide additional spectral purity, the center of the tone bursts can be selected and a Fast Fourier Transform (FFT) can be performed.

The output of the oscilloscope 248 is calibrated with a series of known amplitude calibration signals matching the frequency of signals inserted through a substitutional signal source 260 (for example, this source can be similar to tone burst generator 204).

The shown system 200 also contains a capacitance meter 264 and an AC voltmeter 256. The switching between the DEUT 216 and capacitance meter 264, and between the bias/coupler 232 and substitutional signal source 260 is symbolically represented by a switch 228.

Figure 3:
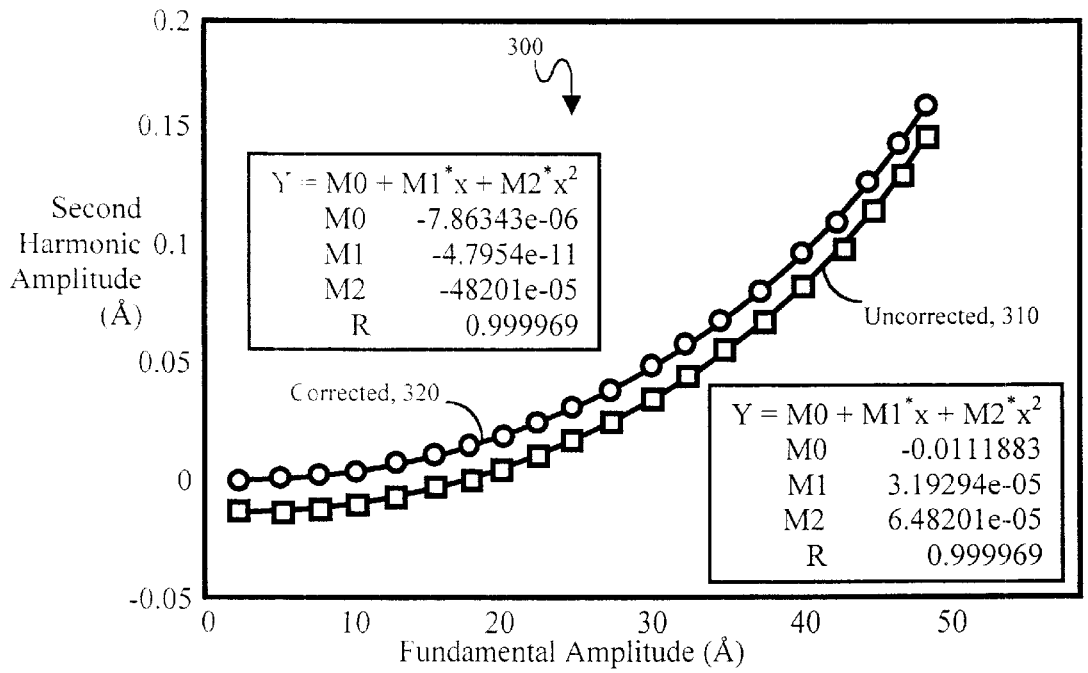
FIG. 3 is a plot of the second harmonic amplitude as a function of the fundamental amplitude for sample measurements using a present-inventive approach (with separate quadratic-fit curves for uncorrected and corrected values).

FIG. 3 shows graphs 300 of the second harmonic amplitude (measured in Angstroms Å) as a function of the fundamental amplitude (also measured in Angstroms Å). The graphs shown are the result of quadratically fitting the uncorrected (310) and corrected (320) data using the following $$A_2 = M_0 + M_1 A_1 + M_2 A_1^2 \quad (10)$$

where $M_0$, $M_1$ and $M_2$ are constants determined by the quadratic fit. The value of $\Gamma$ from Equation 9 is therefore $$\Gamma = M_2 \quad (11)$$

and the offset corrections are given by $$A_{1-offset} = -M_1/2M_2 \quad (12)$$

$$A_{2-offset} = M_0 - [(M_1/2M_2)^2]M_2 \quad (13)$$

It has been observed that offsets typically are not needed for field measurements regarding test materials. Consequently, only the constant $M_2$ is typically used, which is adequate since $M_2$ has been shown to be immune to instrument offsets when the amplifiers used operate in the linear range.

Variations and modifications of the present invention are possible, given the above description. However, all variations and modifications which are obvious to those skilled in the art to which the present invention pertains are considered to be within the scope of the protection granted by this Letters Patent.

For example, the free end of the dielectric material 118 of the DEUT 116 need not be flat, but can be curved to match the characteristics of a non-planar test material surface. Those skilled in the art will appreciate, however, that a newpath analysis may then be needed for valid interpretation of the results. Also, if the surface area of the free end of the dielectric material 118 differs from the surface area of the plate 117, then a new path analysis may be needed.

What is claimed is:

1. A system for measuring acoustic nonlinearity ($\beta$) in test materials, said system comprising:

an acoustic signal generator adapted to apply an acoustic signal to a test material;

a dielectric electrostatic ultrasonic transducer (DEUT) comprising a plate member and a dielectric member coupled to said plate member, said dielectric member being a high dielectric constant insulator, and being adapted to convert received ultrasonic energy into an output electrical signal; and a measurement system coupled to said DEUT, said measurement system being adapted to calculate said nonlinearity $\beta$ in response to the output signal from said DEUT;

wherein said DEUT is adapted to be loosely mounted to a surface of said test material, and said DEUT is adapted to receive acoustic energy from the surface of said test material.

2. The system of claim 1, wherein said insulator is ferroelectric.

3. The system of claim 1, further comprising a supply voltage adapted to bias said DEUT with a DC bias voltage.

4. The system of claim 1, wherein said acoustic signal generator comprises:

a tone burst generator; and a signal amplifier.

5. The system of claim 4, wherein said acoustic signal generator further comprises a bandpass filter.

6. The system of claim 5, wherein said acoustic signal generator further comprises an impedance matching network.

7. The system of claim 1, wherein said measurement system further comprises:

a bias/coupler circuit adapted to separate from the signal output by said DEUT, the AC portion of said output from a DC bias voltage.

8. The system of claim 7, wherein said measurement system further comprises:

a bandpass amplifier coupled to the output of said bias/coupler circuit.

9. The system of claim 8, wherein said measurement system further comprises:

a digital oscilloscope coupled to said bandpass amplifier, said digital oscilloscope adapted to digitize and measure the output of the signal received from said bandpass amplifier.

10. The system of claim 1, wherein said measurement system further comprises:

a control computer adapted to control the operation of said measurement system.

11. A method of measuring acoustic nonlinearity ($\beta$) in test materials, said method comprising the steps of:

generating and applying an acoustic signal to a test material;

providing a dielectric electrostatic ultrasonic transducer (DEUT) comprising a plate member and a dielectric member coupled to said plate member, said dielectric member being a high dielectric constant insulator, and being adapted to convert received ultrasonic energy into an output electrical signal;

loosely mounting said DEUT to a surface of said test material;

via said DEUT, receiving acoustic energy from the surface of said test material; and via a measurement system coupled to said DEUT, calculating said nonlinearity β in response to the output signal from said DEUT.

12. The method of claim 11, wherein said insulator is ferroelectric.

13. The method of claim 11, further comprising the step of:

via a supply voltage, biasing said DEUT with a DC bias voltage.

* * * * *